United States Patent
Bille

(10) Patent No.: US 7,232,436 B2
(45) Date of Patent: Jun. 19, 2007

(54) CLOSED LOOP CONTROL FOR INTRASTROMAL WAVEFRONT-GUIDED ABLATION WITH FRACTIONATED TREATMENT PROGRAM

(76) Inventor: Josef Bille, Hermann Loens Weg, 44/1, 69118 Heidelberg (DE)

( * ) Notice: Subject to any disclaimer, the term of this patent is extended or adjusted under 35 U.S.C. 154(b) by 276 days.

(21) Appl. No.: 11/033,967

(22) Filed: Jan. 12, 2005

(65) Prior Publication Data

US 2005/0149005 A1   Jul. 7, 2005

Related U.S. Application Data

(63) Continuation-in-part of application No. 10/293,226, filed on Nov. 13, 2002, now Pat. No. 6,887,232.

(51) Int. Cl.
*A61B 18/20* (2006.01)

(52) U.S. Cl. .................. 606/5; 606/4; 606/10; 606/12; 351/212; 128/898

(58) Field of Classification Search ................ 606/4–6, 606/10–12, 17, 18; 351/204–206; 128/898
See application file for complete search history.

(56) References Cited

U.S. PATENT DOCUMENTS

| | | | |
|---|---|---|---|
| 4,391,275 A | 7/1983 | Fankhauser et al. | |
| 4,718,418 A | 1/1988 | L'Esperance, Jr. | |
| 4,721,379 A | 1/1988 | L'Esperance | |
| 4,770,172 A | 9/1988 | L'Esperance, Jr. | |
| 4,907,586 A | 3/1990 | Bille et al. | |
| 4,988,348 A | 1/1991 | Bille | |
| 5,777,719 A * | 7/1998 | Williams et al. ............. 351/212 |
| 6,050,687 A | 4/2000 | Bille et al. | |
| 6,095,651 A | 8/2000 | Williams et al. | |
| 6,210,401 B1 * | 4/2001 | Lai .............................. 606/12 |
| 6,220,707 B1 * | 4/2001 | Bille .......................... 351/212 |
| 6,413,251 B1 * | 7/2002 | Williams ....................... 606/5 |
| 6,428,533 B1 * | 8/2002 | Bille ............................ 606/11 |
| 6,887,232 B2 * | 5/2005 | Bille ............................. 606/5 |
| 2004/0092914 A1 | 5/2004 | Bille | |
| 2005/0245915 A1 * | 11/2005 | Loesel et al. ................... 606/4 |

FOREIGN PATENT DOCUMENTS

EP    1 419 752 A1    5/2004

* cited by examiner

*Primary Examiner*—A. Farah
(74) *Attorney, Agent, or Firm*—Nydegger & Associates

(57) ABSTRACT

A closed-loop control system for altering the optical characteristics of a patient's cornea includes an algorithm for predicting the shape of the cornea after one or more gas bubbles resulting from intrastromal photoablation have collapsed. Patient data can be used as an input for the algorithm, which is then run to prepare an initial treatment plan for a corneal alteration. The initial plan typically includes a plurality of intrastromal photoablation locations and corresponding ablation energies. After photoablation of plan location(s) and before the resulting bubbles collapse, a real-time wavefront shape for light passing through the cornea is measured. The wavefront is then used in the algorithm to predict a post bubble collapse cornea shape and to generate an updated treatment plan. The procedure then continues by ablating location(s) identified in the updated treatment plan. Wavefront measurement and plan updating can be repeated as many times as desired.

19 Claims, 5 Drawing Sheets

CLOSED LOOP CONTROL FOR INTRASTROMAL WAVEFRONT-GUIDED ABLATION WITH FRACTIONATED TREATMENT PROGRAM

This application is a continuation-in-part of application Ser. No. 10/293,226 filed Nov. 13, 2002, now U.S. Pat. No. 6,887,232. The contents of application Ser. No. 10/293,226 are incorporated herein by reference.

FIELD OF THE INVENTION

The present invention pertains generally to laser systems that photoablate corneal tissue to improve the visual acuity of an eye. More particularly, the present invention pertains to laser systems and methods that perform intrastromal photoablation of tissue during corrective optical surgery. The present invention is particularly, but not exclusively, useful as a real-time, closed-loop control system which measures the effect of photoablation during a procedure and uses the measured data to update a photoablation treatment plan during the procedure.

BACKGROUND OF THE INVENTION

It is well known that the optical characteristics of an eye can be altered through laser surgery. For example, U.S. Pat. No. 6,050,687 which issued to Bille et al. for an invention entitled "Method and Apparatus for Measuring the Refractive Properties of the Human Eye," discloses a laser system that can be used for such purposes. In any event, a consequence of photoablation, is that individual cells in the tissue are vaporized. Gas is, therefore, a product of photoablation. When a surgical laser procedure involves the superficial photoablation of tissue, the fact that such gases are created does not cause much of a problem. This is not the case, however, when internal tissue is photoablated.

For specific surgical procedures that involve the intrastromal photoablation of corneal tissue, it is known that such photoablation results in the formation of tiny bubbles in the stroma. Further, it is known that the formation of these bubbles introduces aberrations that change the optical characteristics of the cornea. The reason for this change is essentially two-fold. First, the gas bubbles have a different refractive index than that of the surrounding stromal tissue. Second, and perhaps more important, the gas bubbles tend to deform the stroma and, thus, they alter its refractive effect on light passing through the cornea. In a controlled surgical procedure these induced aberrations must be accounted for.

Wavefront analysis provides a useful and helpful conceptual tool for determining the effect a particular medium or material (e.g. the cornea of an eye) will have on a light beam, as the beam passes through the medium (material). For wavefront analysis, a light beam can be conveniently considered as being a so-called "bundle" of component light beams. These component light beams are all mutually parallel to each other, and when all of the component beams of a light beam are in phase with each other as they pass through a plane in space, it is said they define a plane wavefront. However, when a light beam passes through a medium, the medium will most likely have a different refractive effect on each of the individual component beams of the light beam. The result is that the phases of the component light beams will differ from each other. When now considered collectively, these component light beams will define something other than a plane wavefront. In summary, a particular wavefront will define the refractive effect a medium, or several media, have had on a light beam.

Insofar as laser surgery is concerned, it is the objective of such surgery to remove unwanted aberrations from the light beams that a patient perceives visually. As implied above, wavefront analysis can be a helpful tool in evaluating and determining the extent to which refractive properties of a cornea may need to be altered or corrected. Indeed, such an analysis has been helpful for surgical procedures involving superficial photoablation. For example, U.S. Pat. No. 6,428,533B1 which issued to Bille for an invention entitled "Closed Loop Control for Refractive Laser Surgery (LASIK)," and which is assigned to the same assignee as the present invention, discloses such a system.

As recognized by the present invention, when intrastromal photoablation is to be performed, and the evaluations and determinations of a wavefront analysis are put into practice, it is desirable to establish control over each individual component beam defining a wavefront. With this control, induced aberrations such as the aberrations mentioned above, can be accurately compensated for, and the overall control of the procedure enhanced.

As further recognized by the present invention, the temporal effect of intrastromal photoablation can be characterized as having three distinct periods. The first period, which typically lasts for about 30-60 minutes after tissue photoablation, is characterized by the presence of a gas bubble in the stroma. The second period, on the other hand, occurs after the gas bubble has collapsed. During this second period, photoablation induced stresses remain in the stromal tissue that previously surrounded the gas bubble. These induced stresses relax during the second period, and, during this relaxation, the curvature of the cornea changes. Eventually, the curvature of the cornea stabilizes. Thus, the onset of the third period corresponds to the time when the induced stresses have relaxed and the shape of the cornea has substantially stabilized. This stable shape, in turn, represents the long-term surgical performance of the ablation. Typically, the third period begins approximately 1-30 days after the ablation.

In general, a single procedure for corneal corrections can require hundreds of intrastromal photoablations, each of which results in the formation of a corresponding gas bubble. For these corneal corrections, a typical laser pulse repetition rate of approximately 10 kHz is used. With this pulse repetition rate, it can be appreciated that some ablations will occur during a procedure before all of the previously created bubbles have collapsed. Indeed, it is typical for the entire procedure to be completed before any of the gas bubbles have fully collapsed. With the above in mind, it is possible to measure a wavefront between successive ablations which is indicative of corneal shape. This real-time information can then be used to update a treatment plan and thereby revise the planned position and size of subsequent ablations during a procedure.

In a complicated procedure such as a corneal reshaping, it would be helpful to predict the long term surgical effect of an ablation (i.e. the eventual corneal shape after bubble collapse and relaxation of photoablation induced stresses). Preferably, this prediction could be made in real-time from a wavefront measurement that is obtained during a procedure (i.e. after an ablation but before the resulting bubble has collapsed). This information could then be used to modify a treatment plan during the procedure, to increase the overall accuracy of the procedure. As recognized by the present invention, however, the relaxation of induced stresses which occurs during the second period described above, and its effect on corneal shape, is somewhat unpredictable. At least this is so using current models. On the other hand, the inventors have determined that it is possible to estimate the corneal shape after bubble collapse (i.e. at the end of the second period described above). Moreover, this can be done with real-time wavefront data measured between successive bubbles during a procedure.

In light of the above, it is an object of the present invention to provide systems and methods suitable for the purposes of using real-time wavefront data measured during an intrastromal photodisruption procedure to improve the surgical performance of the procedure. It is another object of the present invention to provide systems and methods for performing an accurate optical correction which accounts for the relatively long-term effects associated with the relaxation of photoablation induced stresses. It is yet another object of the present invention to provide systems and methods for intrastromal photoablation which are easy to use, relatively simple to implement, and comparatively cost effective.

SUMMARY OF THE INVENTION

In a first aspect of the present invention, a closed-loop system is provided which will control the photoablation of stromal tissue in an eye during an intrastromal surgical procedure. More specifically, in addition to controlling the photoablation of the stromal tissue that is necessary for a corrective procedure, the control system of the present invention also compensates for optical aberrations that are induced by gas bubbles as they form in the stromal tissue that is being photoablated.

For purposes of wavefront analysis, a light beam is properly considered as including a plurality of individual component beams. Collectively, these constituent component light beams define a wavefront for the larger inclusive light beam. With this in mind, and in the context of the present invention, several definitions for light beam wavefronts are helpful. Specifically, these definitions pertain after a light beam has passed through the stroma of an eye. A "desired wavefront" results from the stroma of a corrected eye, and is the objective of a surgical procedure. A "distorted wavefront" results from the stroma of an uncorrected eye, and exhibits the actual real-time characteristics of the cornea, before correction. An "induced wavefront" results from the formation of bubbles in the stroma, and includes the "distorted wavefront." A "rectified wavefront" results by incorporating an "induced wavefront" with a "desired wavefront."

Structurally, the system of the present invention includes two distinct laser sources. One is for generating an ablation laser beam that will be used to photoablate stromal tissue. The other is for generating a diagnostic laser beam. Conceptually, as mentioned above, the diagnostic laser beam is properly considered as including a plurality of individual component beams.

Along with the two laser sources just mentioned, the system typically includes an active mirror and a detector. More specifically, the active mirror comprises a plurality of separate reflective elements for individually reflecting respective component beams of the diagnostic beam. Together, these elements of the active mirror are used, in concert, to direct the diagnostic laser beam to a focal spot on the retina of the eye. The detector is then used to receive the diagnostic beam after it has been reflected from the retina.

In the operation of the present invention, a compensator incorporates a desired wavefront (predetermined for the patient), with the induced wavefront as it is received by the detector. This incorporation creates a rectified wavefront. A comparator is then used to compare the rectified wavefront with the distorted wavefront (diagnostically predetermined) to create an error signal. Consistent with the wavefront analysis used to define light beams, the error signal is properly considered as having a plurality of error segments. These error segments are then used by the system of the present invention to individually activate a respective reflective element of the active mirror, and to thereby maintain the focal spot of the diagnostic beam on the retina. The ablative laser source can then be continuously operated to photoablate stromal tissue using a so-called "spot-by-spot" local ablation strategy until the error signal is substantially a nullity.

In another aspect of the present invention, a system and method are disclosed for altering the optical characteristics of a patient's cornea that uses an algorithm to predict a post photoablation corneal shape. More specifically, the algorithm is developed to predict the shape of the cornea after one or more gas bubbles resulting from intrastromal photoablation have collapsed. In greater detail, patient data is used as an input for the algorithm, which is then run to prepare an initial treatment plan to alter the optical characteristics of the patient's cornea. As an output from the algorithm, the initial treatment plan typically includes a plurality of intrastromal photoablation locations and a respective ablation energy for photoablation at each location.

Once the initial treatment plan is prepared, the next step is to photoablate tissue at one or more locations in accordance with the plan. Each photoablation then creates a respective gas bubble in the stroma. After one or more locations have been photoablated and before the resulting bubbles collapse, a real-time wavefront shape for light passing through the cornea is measured. Typically, for this real-time wavefront measurement, light passing through a gas bubble is not used. Instead, a portion of the cornea that has not undergone photoablation can be used to establish the real-time wavefront.

Once measured, the real-time wavefront can be input into the algorithm to predict a post bubble collapse shape for the cornea in its current, mid-procedure state. This prediction is then used with the algorithm to generate a real-time updated treatment plan. The procedure then continues by ablating one or more locations identified in the updated treatment plan. After one or more locations of the updated plan are photoablated, another wavefront measurement is conducted and the wavefront is processed to yield yet another real-time updated treatment plan. This cycle is then continued as many times as necessary until a suitable photoablation has been obtained.

In greater analytical detail, a number of factors can be measured or characterized for input into the algorithm to predict a post bubble collapse wavefront. For example, the pre-existing stress distribution in the patient's cornea will effect the post bubble collapse shape of the cornea after an intrastromal photoablation. Thus, data corresponding to a measured stress distribution can be input into the algorithm to predict a post bubble collapse wavefront shape. In addition, the algorithm can account for several events which occur over time after an ablation. These can include, but are not limited to, water evaporation, tissue expansion, extension of collagen fibers and collapse of tissue.

In yet another aspect of the present invention, a fractionated treatment program for accurately correcting an optical deficiency using intrastromal photoablation is provided. In particular, the fractionated treatment program is designed to account for the relatively long-term effects associated with the relaxation of photoablation induced stresses. In greater detail, the fractionated treatment program involves a plurality of temporally spaced apart procedures wherein photoablation induced stresses are allowed to relax between procedures. Typically, each of the procedures is conducted in accordance with the disclosure provided above in which an algorithm is used to provide updated treatment plans during a procedure.

In more detail, for the first procedure in the fractionated treatment program, a laser beam is directed to a focal point at a subsurface location and scanned to photoablate stromal tissue at a plurality of locations. In one implementation, this procedure is conducted according to a treatment plan that is updated during the procedure as described above. In a particular implementation, the treatment plan that is used for the first procedure is designed to leave the cornea in an undercorrected state. Specifically, the goal is to leave the cornea in an undercorrected state at the end of the procedure and after the bubbles that were created during the procedure have collapsed. Next, for the fractionated treatment program, a predetermined time period is allowed to elapse after the first procedure. During this time period there is no photoablation. Instead, the tissue that was stressed by photoablation is allowed to relax to a substantially stable condition. This results in a relatively stable corneal shape. Typically, the elapsed period is between approximately 1 day and approximately 30 days.

After the shape of the cornea has stabilized from the first photoablation procedure, as indicated above, the cornea is typically in an undercorrected state. A second photoablation procedure is then performed. This second procedure is also typically conducted in accordance with a treatment plan that is updated during the procedure, and again typically leaves the cornea in an undercorrected state. Once again, the resulting photoablation induced stresses are allowed to relax until a stable corneal shape is reached (e.g. 1-30 days). Any number of such intermediate procedures, each predictably leaving the cornea in an undercorrected state, can be performed. Thereafter, a final procedure is performed having a treatment plan that is designed to leave the cornea in a fully corrected state.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
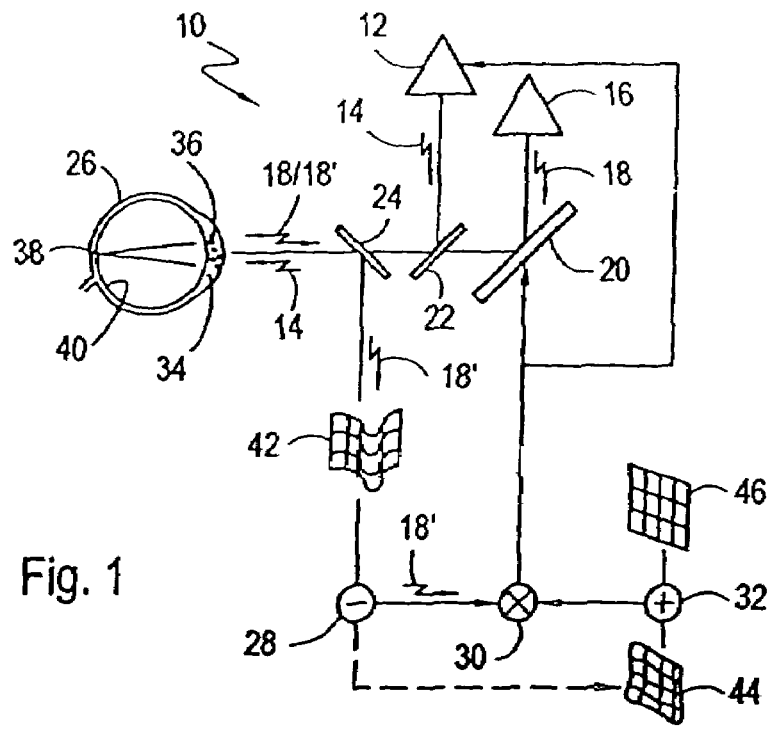
FIG. 1 is a schematic layout showing the interrelationships of components in a system for controlling the intrastromal photoablation of corneal tissue in an eye in accordance with the present invention.

Referring initially to FIG. 1, a closed-loop system for intrastromal photoablation of corneal tissue in accordance with the present invention is shown and is generally designated 10. In detail, the components of system 10 include a source 12 for generating an ablation laser beam 14, and a source 16 for generating a diagnostic laser beam 18. Further, the system 10 includes an active, multi-facet mirror 20, a beam splitter 22 and a beam splitter 24. More particularly, the active mirror 20 is preferably of a type disclosed in U.S. Pat. No. 6,220,707 which issued to Bille for an invention entitled "Method for Programming an Active Mirror to Mimic a Wavefront" and which is assigned to the same assignee as the present invention. As shown, the active mirror 20 and the beam splitters 22 and 24 direct the diagnostic laser beam 18 from diagnostic laser source 16 toward an eye 26. Likewise, the beam splitters 22 and 24 are used to direct the ablation laser beam 14 from the ablation laser source 12 toward the eye 26.

FIG. 1 also shows that the system 10 of the present invention includes a detector 28, a comparator 30 and a compensator 32. In particular, the detector 28 is preferably of a type commonly known as a Hartmann-Shack sensor. The comparator 30 and compensator 32 are electronic components known in the pertinent art that will perform the requisite functions for the system 10.

Still referring to FIG. 1, it is to be appreciated and understood that during an intrastromal photoablation procedure, as performed by the system 10 of the present invention, the ablation laser beam 14 is focused (by optical components not shown) onto stromal tissue 34 in the cornea of the eye 26 for the purpose of accomplishing intrastromal photoablation. A consequence of this photoablation of the tissue 34 is the formation of gas bubbles 36 that introduce optical aberrations in the stromal tissue 34. At the same time, the diagnostic laser beam 18 is focused (by optical components not shown) to a focal spot 38 on the retina 40 of the eye 26. In this combination, control by the system 10 over the ablation laser beam 14 is actually accomplished using the reflected diagnostic laser beam 18', as it is reflected through the stromal tissue 34 from the focal spot 38 on the retina 40 of eye 26.

FIG. 1 shows that as the reflected diagnostic laser beam 18' exits from the eye 26 through the stromal tissue 34, the beam 18' is directed by beam splitter 24 toward the detector 28. Using wavefront analysis considerations, the reflected diagnostic beam 18' can be conceptually considered as including a plurality of individual and separate laser beam components. Together, these components can be characterized as a distorted wavefront 42. Further, this distorted wavefront 42 will result from two contributions. One contribution results from the uncorrected eye 26 and is an actual real-time consequence of light passing through the stromal tissue 34. It is this contribution that is to be corrected. The other contribution results from the aberrations that are introduced by the presence of the gas bubbles 36 in the stromal tissue 34. Again using wavefront analysis, the contribution introduced by the gas bubbles 36 can be conceptualized as a wavefront having a plurality of components that are collectively characterized as an induced wavefront 44 which includes transient components (bubbles) and permanent void components, the relative proportions of which can be estimated using empirical data collected before the procedure. FIG. 1 further shows a desired wavefront 46 after photoablation bubbles have collapsed. This desired wavefront 46 will most likely be either a plane wavefront, or a wavefront that is relatively similar to a plane wavefront. In any event, it is the desired wavefront 46 that is the objective of the procedure to be performed by the system 10.

Figure 2:
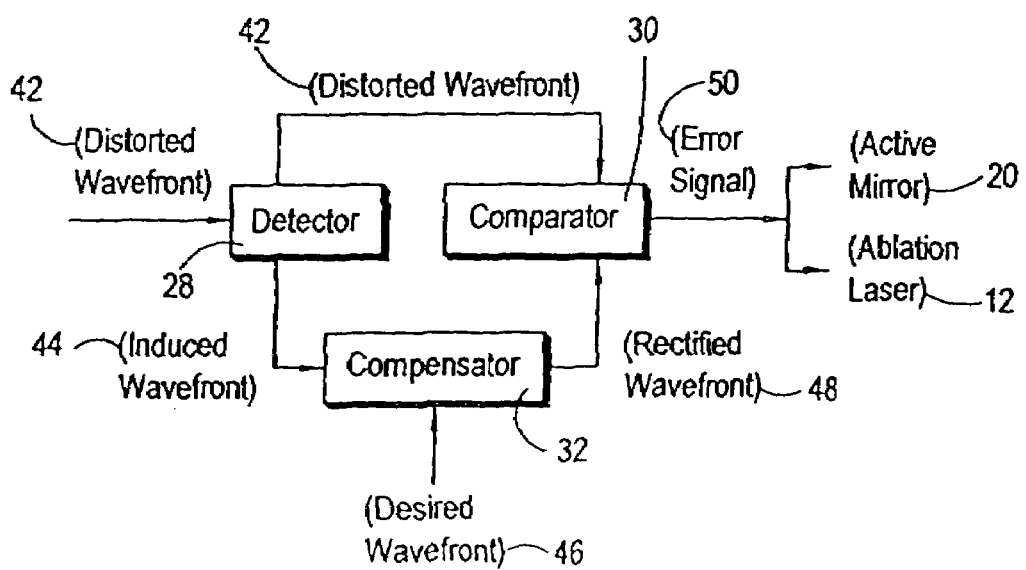
FIG. 2 is a functional representation of the wavefront analysis techniques used in the operation of the system of the present invention.

By cross referencing FIG. 1 with FIG. 2, it will be appreciated that in the operation of the system 10, the distorted wavefront 42 is first received by the detector 28. Using predetermined diagnostic information about the corrections that are to be made to the eye 26 by system 10, the detector 28 determines and generates the induced wavefront 44. The compensator 32 then augments the desired wavefront 46 with the bubble component of the induced wavefront 44. This alteration creates a rectified wavefront 48. The rectified wavefront 48 is then compared with the distorted wavefront 42 to generate an error signal 50. In turn, this error signal 50 is used to manipulate the active mirror 20 for control of the diagnostic laser beam 18. Importantly, the error signal 50 is also used to activate the ablation laser source 12 and, specifically, the error signal 50 causes the ablation laser source 12 to cease its operation when the error signal 50 is a nullity.

Figure 3:
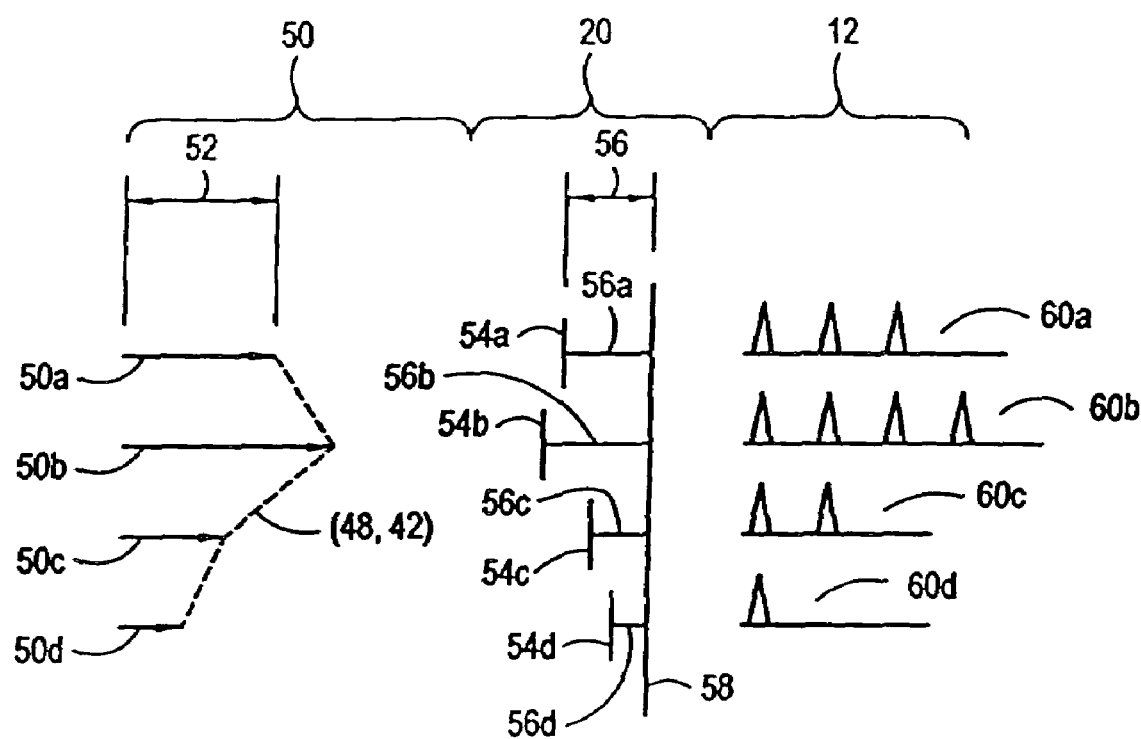
FIG. 3 is a schematic representation of the interrelationships between the component beams of a wavefront, corresponding reflective elements of the active mirror, and required laser pulses from the ablation laser source.

In response to the error signal 50, the operation of the active mirror 20, as well as the operation of ablation laser source 12 will, perhaps, be best appreciated with reference to FIG. 3. Again, using a wavefront analysis, the error signal 50 can conceptually be considered as comprising a plurality of component error signals. For this analysis, the component error signals 50a, 50b, 50c and 50d shown in FIG. 3 are only exemplary. In general, what is important here, is that each of the exemplary component error signals 50a-d result from the interaction of corresponding components of the wavefronts 42, 44, 46 and 48. As disclosed above, these wavefronts 42, 44, 46 and 48 directly result from the refraction of corresponding beam components of the diagnostic laser beam 18. Stated differently, each component beam of the diagnostic laser beam 18 is present in each of the wavefronts: namely, the distorted wavefront 42, the induced wavefront 44, the desired wavefront 46, and the rectified wavefront 48. Consequently, each component beam of the diagnostic laser beam 18 generates a corresponding error signal component 50a-d. Depending on its refractive history as it passes through the system 10, each error signal component 50a-d will have a respective magnitude 52.

FIG. 3 also indicates that the active mirror 20 includes a plurality of reflective elements 54, of which the reflective elements 54a-d are exemplary. FIG. 3 also indicates that each reflective element 54 is at a respective distance 56 (i.e. distances 56a-d) from a datum 58. For example, each error signal component 50 (e.g. error signal component 50a) is used by the system 10 to establish a respective distance 56 for a corresponding reflective element 54 of the active mirror 20 (e.g. signal 50a and distance 56a).

FIG. 3 also shows that the ablation laser source 12 will generate a plurality of separate laser pulse trains 60 that correspond to each corresponding error signal component 50a-d. For instance, the error signal component 50a, will generate a laser pulse train 60a. The laser pulse train 60a is then continued until the error signal component 50a is a nullity. Similarly, the pulse trains 60b-d react to corresponding error signal components 50b-d. While this is happening to ablate the stromal tissue 34, the error signal components 50a-d also interact with the active mirror 20. Specifically, as the error signal component 50a decreases in its magnitude 52, the distance 56 of reflective element 54a from datum 58 also decreases. This is done to maintain the focal spot 38 fixed on the retina 40 of eye 26 so that the distorted wavefront 42 is maintained as an accurate measure of the progress of the intrastromal photoablation procedure. The ablation laser source 12 is inactivated, when all of the error signal components 50a-d (i.e. error signal 50) are a nullity.

Figure 4:
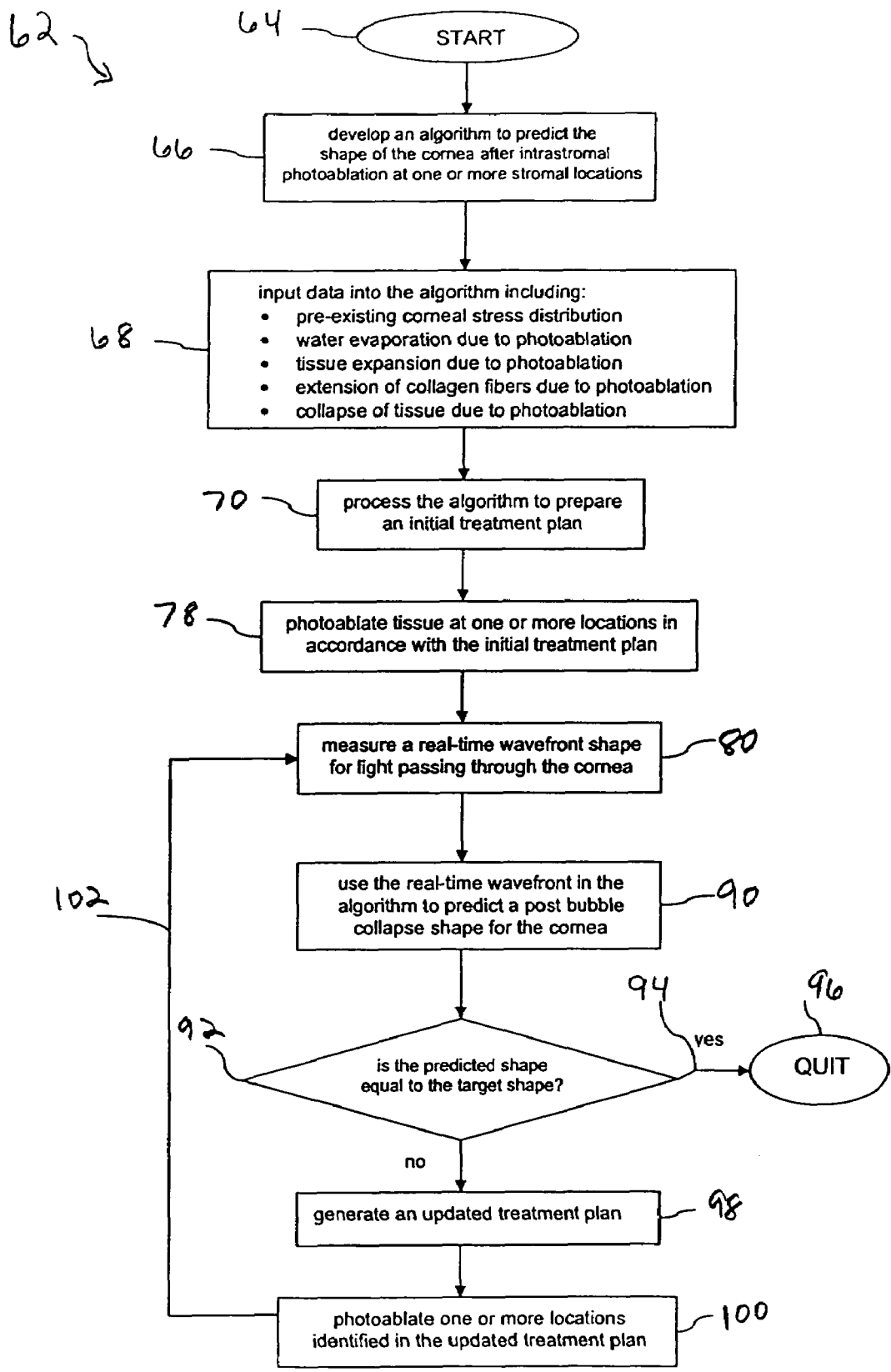
FIG. 4 is a logic flow diagram illustrating a method for updating a treatment plan during a procedure using real-time wavefront measurements that are conducted during the procedure.

FIG. 4 illustrates a procedure (designated generally 62) for intrastromal photoablation that uses real-time wavefront measurements (i.e. measurements that are conducted during the procedure) to periodically update a photoablation treatment plan during the procedure. The procedure starts (symbol 64) by diagnosing an optical deficiency in a patient and prescribing a targeted, post procedure corneal shape. As detailed further below, the targeted shape may correspond to a fully corrected or partially corrected (i.e. undercorrected) corneal shape. As shown in FIG. 4, the procedure also includes the step of developing an algorithm to predict a post photoablation corneal shape (box 66). Once developed, input data for use in an algorithm can include, but is not necessarily limited to, one or more of the following inputs: a measured corneal stress distribution, water evaporation which occurs during and after photoablation, tissue expansion, extension of collagen fibers and collapse of tissue (box 68).

For the procedure 62, the algorithm is developed to predict the shape of the cornea after one or more gas bubbles resulting from a portion or all of intrastromal photoablation procedure 62 have collapsed. With this capability, the algorithm can be used to prepare an initial treatment plan to alter the optical characteristics of the patient's cornea (box 70). As an output from the algorithm, the initial treatment plan typically includes a plurality of intrastromal photoablation locations and a respective ablation energy for photoablation at each location.

Figure 5:
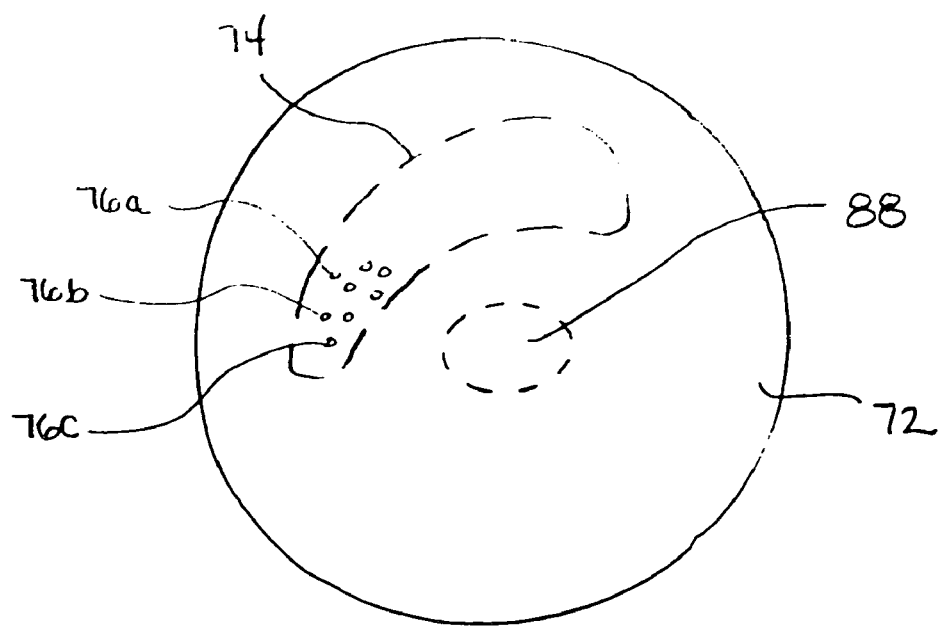
FIG. 5 is a top plan view of a cornea showing an intrastromal photoablation treatment area and an area for diagnostic monitoring during a photoablation procedure.

FIG. 5 shows a cornea 72 and illustrates an initial treatment plan that includes a treatment area 74 which typically includes hundreds of photoablation locations 76, of which locations 76a-c have been labeled. For the procedure, the initial treatment plan typically specifies both the locations 76 and a photoablation energy for each location 76. This photoablation energy may be the same for all locations 76 or may vary from location 76 to location 76. Referring back to FIG. 4, it can be seen that after the initial treatment plan is prepared (box 70), the next step is to photoablate tissue at one or more locations in accordance with the plan (box 78). Each photoablation then creates a respective gas bubble in the stroma. These gas bubbles collapse after about 30 to 60 minutes. It is to be appreciated that each gas bubble severely distorts a wavefront passing through the cornea 72 and that the shape of the cornea 72 before the bubble collapses is significantly different than the shape of the cornea 72 after the bubble collapses.

Figure 6:
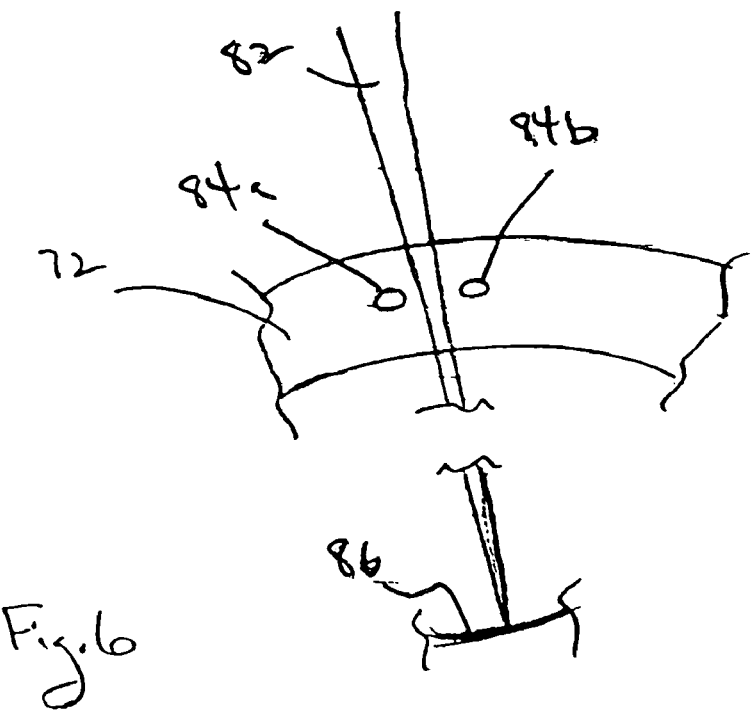
FIG. 6 is a schematic diagram showing a cross-section of an eye to illustrate a diagnostic beam that is passed between photoablation bubbles and focused on the retina of the eye.

Continuing with FIG. 4, it is shown that once one or more locations have been photoablated, and before the resulting bubbles collapse, a real-time wavefront shape for light passing through the cornea 72 is measured (box 80). Typically, as illustrated by FIGS. 5 and 6, light that passes through a gas bubble 84a,b is not used to measure the real-time wavefront. Instead, as best seen in FIG. 6, a diagnostic laser beam 82 is passed through the cornea 72 between bubbles 84a,b to a focal point on the retina 86, as shown. This focal point then acts as a point source of light. As such, light from the focal point on the retina 86 passes back through the cornea 72. As shown in FIG. 5, light from the retina 86 (best seen in FIG. 6) that passes through a portion of the cornea 72 (i.e. diagnostic area 88 that has not undergone photoablation) can be used to measure a real-time wavefront for the cornea 72. In some cases, light passing through the photoablation area 74 or at the edge of the photoablation area 74 can be used to measure a real-time wavefront.

Once measured, FIG. 4 shows that the real-time wavefront can be input into the algorithm to predict a post bubble collapse shape for the cornea 72 (box 90). This post bubble collapse shape represents a corneal shape after the bubbles that have been created thus far in the procedure have collapsed. A processor then compares the predicted post bubble collapse shape with the target corneal shape (decision box 92). If the predicted post bubble collapse shape and the target corneal shape are substantially the same (arrow 94), then the procedure is over (symbol 96). On the other hand, if the predicted post bubble collapse shape and the target corneal shape are not the same, an updated treatment plan is generated (box 98). Specifically, the predicted post bubble collapse shape is used with the algorithm to generate the updated treatment plan. Like the initial treatment plan, the real-time updated treatment plan includes a plurality of new photoablation locations and a corresponding photoablation energy for each new location.

FIG. 4 shows that the procedure 62 continues by ablating one or more locations identified in the updated treatment plan (box 100). After one or more locations of the updated plan are photoablated, arrow 102 shows that another wavefront measurement is conducted (box 80) and used to predict a post bubble collapse shape for the cornea 72 (box 90). A processor then compares the predicted post bubble collapse shape with the target corneal shape (decision box 92). If the predicted post bubble collapse shape and the target corneal shape are not the same, an updated treatment plan is generated (box 98) and one or more locations in the updated plan are photoablated (box 100). As shown, this cycle (i.e. boxes 80, 90, 92, 98 and 100) is then continued as many times as necessary until the predicted corneal shape and the target corneal shape are substantially the same.

Figure 7:
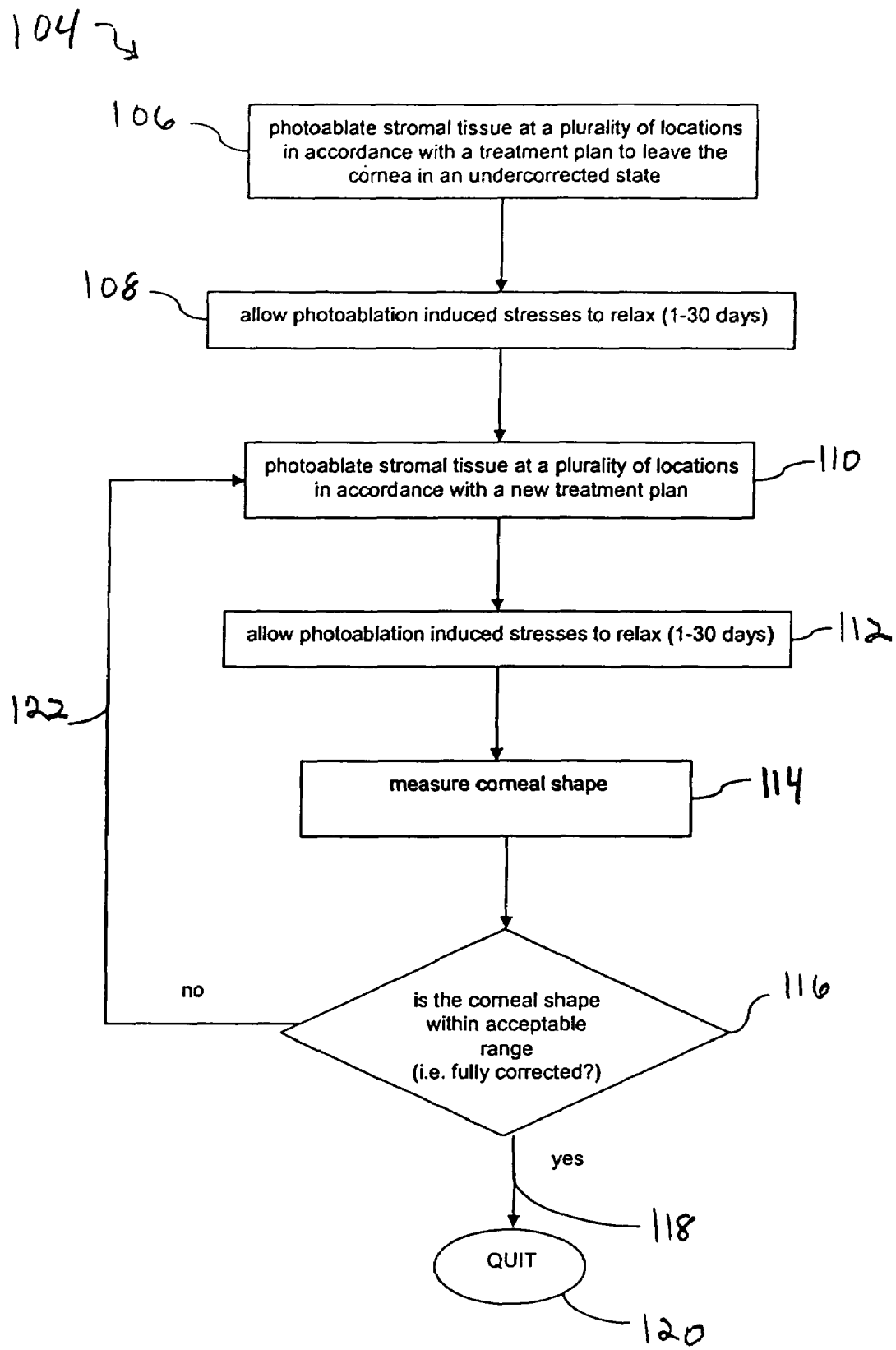
FIG. 7 is a logic flow diagram illustrating a fractionated treatment program for accurately altering the optical characteristics of a cornea.

FIG. 7 is a logic flow diagram illustrating a fractionated treatment program (designated generally 104) for accurately altering the optical characteristics of a cornea using intrastromal photoablation. Functionally, the fractionated treatment program 104 is designed to account for the relatively long-term effects associated with the relaxation of photoablation induced stresses. As shown in FIG. 7, the fractionated treatment plan includes a first procedure in which a laser beam is directed to a focal point at a subsurface location and scanned to photoablate stromal tissue at a plurality of locations (box 106). In one implementation of the fractionated treatment plan 104, this first procedure is conducted according to a treatment plan that is updated during the procedure as shown in FIG. 4 and described above. In a particular implementation, the treatment plan used for the procedure is designed to leave the cornea in an undercorrected state at the end of the procedure (i.e. in an undercorrected state after bubbles created during the procedure have collapsed). Next, as shown in FIG. 7, a predetermined time period is allowed to elapse without photoablation (box 108). During this time period, tissue that was stressed by photoablation, including tissue surrounding the gas bubbles, is allowed to relax to a substantially stable condition resulting in a relatively stable corneal shape. Typically, the elapsed period is between approximately 1 day and approximately 30 days.

After the shape of the cornea has stabilized from the first photoablation procedure, box 110 in FIG. 7 indicates that another photoablation procedure is performed. This second procedure can also be conducted according to a treatment plan that is updated during the procedure as shown in FIG. 4 and described above. In addition, the second procedure can be designed to leave the cornea in an uncorrected state or can be designed to try to place the cornea in a fully corrected state. FIG. 7 shows that after the second procedure, the resulting photoablation induced stresses are allowed to relax approximately 1-30 days until a stable corneal shape is reached (box 112). The next step is to measure the shape of the cornea (box 114), for example, using wavefront analysis or some other appropriate diagnostic tool. The measured shape is then verified to see whether it is within an acceptable range wherein the eye is considered to be "fully corrected" (decision box 116). If the measured shape is within an acceptable range (arrow 118), then the procedure is over (symbol 120). On the other hand, if the measured shape is not within an acceptable range (arrow 122), then FIG. 7 shows that another photoablation procedure is performed (box 110).

Each additional procedure (box 110) can be designed to leave the cornea in an uncorrected state or can be designed to try to place the cornea in a fully corrected state. FIG. 7 shows that after each procedure (box 110), the resulting photoablation induced stresses are allowed to relax (box 112), a corneal shape is measured (box 114), and the measured shape is then verified to see whether it is within an acceptable range wherein the eye is considered to be "fully corrected" (decision box 116). This cycle (boxes 110, 112, 114 and 116) can be continued as many times as necessary until the measured corneal shape is in the acceptable range. In one particular implementation, approximately ten procedures are conducted with the first nine designed to leave the cornea in an undercorrected state. A final procedure is then performed having a treatment plan that is designed to leave the cornea in a fully corrected state.

While the particular Closed Loop Control for Intrastromal Wavefront-Guided Ablation with Fractionated Treatment Program as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for altering the optical characteristics of a patient's cornea, said method comprising the steps of:

preparing an algorithm to predict a shape for the cornea after collapse of a gas bubble resulting from an intrastromal photoablation;

inputting patient data into said algorithm to prepare an initial treatment plan to alter the optical characteristics of the patient's cornea, said initial treatment plan including at least one photoablation location;

photoablating a location in the initial treatment plan to create a gas bubble;

measuring a wavefront shape for light passing through the cornea after said photoablation step and before said gas bubble collapses;

processing said algorithm with said measured wavefront shape to generate an updated treatment plan, said updated treatment plan including at least one photoablation location; and using a laser beam to photoablate tissue at a location in the updated treatment plan.

2. A method as recited in claim 1 wherein said method further comprises the steps of:

measuring a stress distribution in the patient's cornea; and inputting data corresponding to said measured stress distribution into said algorithm to predict a post bubble collapse wavefront shape.

3. A method as recited in claim 1 wherein the intrastromal photoablation causes water evaporation and said method comprises the step of inputting data corresponding to said water evaporation in predicting a post bubble collapse wavefront shape.

4. A method as recited in claim 1 wherein the intrastromal photoablation causes tissue expansion and said method comprises the step of inputting data corresponding to said tissue expansion in predicting a post bubble collapse wavefront shape.

5. A method as recited in claim 1 wherein the intrastromal photoablation causes extension of collagen fibers and said method comprises the step of inputting data corresponding to said extension of collagen fibers in predicting a post bubble collapse wavefront shape.

6. A method as recited in claim 1 wherein the intrastromal photoablation causes collapse of tissue and said method comprises the step of inputting data corresponding to said collapse of tissue in predicting a post bubble collapse wavefront shape.

7. A method as recited in claim 1 wherein said measuring step measures said wavefront shape using light that has not passed through a gas bubble.

8. A system for altering the optical characteristics of a patient's cornea, said system comprising:

a software equipped computer for processing an algorithm to predict a shape for the cornea after collapse of a gas bubble resulting from an intrastromal photoablation;

a means for inputting patient data into said computer for use with said algorithm to prepare an initial treatment plan, said initial treatment plan including at least one photoablation location to alter the optical characteristics of the patient's cornea;

a laser means responsive to said computer for photoablating a location in the initial treatment plan to create a gas bubble;

a means for measuring a wavefront shape for light passing through the cornea after photoablation of said location and before a resulting gas bubble collapses;

a means for inputting said measured wavefront shape into said algorithm to generate an updated treatment plan, said updated treatment plan including at least one photoablation location; and a means responsive to said computer to configure said laser means to photoablate a location in the updated treatment plan.

9. A system as recited in claim 8 wherein said laser means generates a pulsed laser beam.

10. A system as recited in claim 8 wherein said measuring means is a Hartmann-Shack sensor unit.

11. A system as recited in claim 8 further comprises:

means for measuring a stress distribution in the patient's cornea; and means for inputting data corresponding to said measured stress distribution into said algorithm to predict a post bubble collapse wavefront shape.

12. A system as recited in claim 8 wherein the intrastromal photoablation causes water evaporation and said system further comprises a means for inputting data corresponding to said water evaporation into said algorithm.

13. A system as recited in claim 8 wherein the intrastromal photoablation causes tissue expansion and said system further comprises a means for inputting data corresponding to said tissue expansion into said algorithm.

14. A system as recited in claim 8 wherein the intrastromal photoablation causes extension of collagen fibers and said system further comprises a means for inputting data corresponding to said extension of collagen fibers into said algorithm.

15. A system as recited in claim 8 wherein the intrastromal photoablation causes collapse of tissue and said system further comprises a means for inputting data corresponding to said collapse of tissue into said algorithm.

16. A method for correcting an optical deficiency in a cornea of an eye, said method comprising the steps of:

directing a laser beam to a focal point at a subsurface location in the cornea to photoablate stromal tissue at the location;

scanning the focal point to successive locations to photoablate stromal tissue at each successive location and temporarily induce stresses in tissue surrounding the locations;

allowing a time period greater than one day to elapse without photoablation after said scanning step, said time period being of sufficient duration to allow said stressed tissue to relax to a substantially stable condition; and thereafter photoablating additional stromal tissue.

17. A method as recited in claim 16 wherein said optical deficiency is undercorrected after said scanning step.

18. A method as recited in claim 16 wherein said photoablating additional stromal tissue step comprises the sub-steps of:

directing a laser beam to a focal point at a subsurface location in the cornea to photoablate stromal tissue at the location;

scanning the focal point to successive locations to photoablate stromal tissue at each successive location and temporarily induce stresses in tissue surrounding the locations;

allowing a predetermined time period to elapse without photoablation after said scanning step, said time period being of sufficient duration to allow said stressed tissue to relax to a substantially stable condition; and thereafter photoablating additional stromal tissue.

19. A method as recited in claim 16 wherein said directing and scanning steps comprise the sub-steps of:

preparing an algorithm to predict a shape for the cornea after collapse of a gas bubble resulting from an intrastromal photoablation;

inputting patient data into said algorithm to prepare an initial treatment plan to alter the optical characteristics of the patient's cornea, said initial treatment plan including at least one photoablation location;

photoablating a location in the initial treatment plan to create a gas bubble;

measuring a wavefront shape for light passing through the cornea after said photoablation step and before said gas bubble collapses;

processing said algorithm with said measured wavefront shape to generate an updated treatment plan, said updated treatment plan including at least one photoablation location; and using a laser beam to photoablate tissue at a location in the updated treatment plan.

* * * * *